(12) United States Patent
Kornet

(10) Patent No.: US 8,386,053 B2
(45) Date of Patent: Feb. 26, 2013

(54) SUBCLAVIAN ANSAE STIMULATION

(75) Inventor: Lilian Kornet, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 350 days.

(21) Appl. No.: 12/262,867

(22) Filed: Oct. 31, 2008

(65) Prior Publication Data

US 2010/0114254 A1    May 6, 2010

(51) Int. Cl.
*A61N 1/00* (2006.01)

(52) U.S. Cl. ............. 607/116; 607/1; 607/2; 607/3

(58) Field of Classification Search .............. 607/1–2, 607/116, 3
See application file for complete search history.

(56) References Cited

U.S. PATENT DOCUMENTS

| | | | |
|---|---|---|---|
| 5,203,326 | A | 4/1993 | Collins |
| 5,344,438 | A | 9/1994 | Testerman et al. |
| 5,817,132 | A | 10/1998 | Karagueuzian et al. |
| 6,292,695 | B1 | 9/2001 | Webster, Jr. et al. |
| 6,449,507 | B1 | 9/2002 | Hill et al. |
| 6,487,446 | B1 | 11/2002 | Hill et al. |
| 6,532,388 | B1 | 3/2003 | Hill et al. |
| 6,564,096 | B2 | 5/2003 | Mest |
| 6,690,973 | B2 | 2/2004 | Hill et al. |
| 6,937,896 | B1 | 8/2005 | Kroll |
| 6,978,174 | B2 | 12/2005 | Gelfand et al. |
| 7,123,961 | B1 | 10/2006 | Kroll et al. |
| 7,139,607 | B1 | 11/2006 | Shelchuk |
| 7,142,917 | B2 | 11/2006 | Fukui |
| 7,142,919 | B2 | 11/2006 | Hine et al. |
| 7,162,303 | B2 | 1/2007 | Levin et al. |
| 7,225,017 | B1 | 5/2007 | Shelchuk |
| 7,245,967 | B1 | 7/2007 | Shelchuk |
| 7,277,761 | B2 | 10/2007 | Shelchuk |
| 7,305,265 | B2 | 12/2007 | Fukui |
| 2001/0000802 | A1 * | 5/2001 | Soykan et al. ............. 623/1.13 |
| 2003/0100924 | A1 | 5/2003 | Foreman et al. |
| 2003/0216792 | A1 | 11/2003 | Levin et al. |
| 2004/0015193 | A1 | 1/2004 | Lamson et al. |
| 2004/0138713 | A1 | 7/2004 | Stickney et al. |
| 2005/0149148 | A1 * | 7/2005 | King ................................. 607/70 |
| 2005/0234523 | A1 | 10/2005 | Levin et al. |
| 2005/0246006 | A1 * | 11/2005 | Daniels ............................ 607/117 |
| 2005/0288730 | A1 | 12/2005 | Deem et al. |
| 2006/0041277 | A1 | 2/2006 | Deem et al. |
| 2006/0111745 | A1 | 5/2006 | Foreman et al. |
| 2006/0111746 | A1 | 5/2006 | Foreman et al. |
| 2006/0212078 | A1 | 9/2006 | Demarais et al. |
| 2006/0265014 | A1 | 11/2006 | Demarais et al. |
| 2007/0100380 | A1 | 5/2007 | Fukui |
| 2007/0173899 | A1 | 7/2007 | Levin et al. |
| 2007/0191895 | A1 | 8/2007 | Foreman et al. |
| 2007/0265687 | A1 | 11/2007 | Deem et al. |

(Continued)

OTHER PUBLICATIONS

Search Report and Written Opinion from corresponding PCT Application Serial No. PCT/US2009/062613 mailed Mar. 10, 2010 (10 pages).

(Continued)

*Primary Examiner* — Nicole F Lavert
(74) *Attorney, Agent, or Firm* — Carol F. Barry

(57) ABSTRACT

Techniques for improving cardiac performance by applying stimulation to the subclavian ansae nerve of a patient are disclosed. In one example, a method comprises identifying a human patient as having a cardiac condition, and delivering stimulation therapy to a subclavian ansae nerve of a human patient with a stimulation electrode.

34 Claims, 8 Drawing Sheets

U.S. PATENT DOCUMENTS

| | | | |
|---|---|---|---|
| 2007/0299476 | A1* | 12/2007 | Park et al. ............................ 607/9 |
| 2008/0021503 | A1* | 1/2008 | Whitehurst et al. ............... 607/3 |
| 2008/0051839 | A1 | 2/2008 | Libbus et al. |
| 2008/0119907 | A1 | 5/2008 | Stahmann |
| 2008/0213331 | A1 | 9/2008 | Gelfand et al. |

OTHER PUBLICATIONS

International Preliminary Report on Patentability, PCT Application Serial No. PCT/US2009/062613, mailed May 12, 2011, 6 pp.

Changfeng Tai et al., "Simulation Analysis of Conduction Block in Unmyelinated Axons Induced by High-Frequency Biphasic Electrical Currents," *IEEE Transactions on Biomedical Engineering*, vol. 52, No. 7 (Jul. 2005) pp. 1323-1332.

Janes RD et al. "Functional and anatomical variability of canine cardiac sympathetic efferent pathways: implications for regional denervation of the left ventricle," *Can J Physiol Pharmacol*. Jul. 1986; 64(7):958-69, Abstract (1 page).

Atul Verma et al., "Pre-implantation B-type nariuretic peptide level is an independent predictor of future appropriate implantable defibrillator therapies," *Heart* published online May 27, 2005 (31 pages).

Donatella Cerati et al., "Single Cardiac Vagal Fiber Activity, Acute Myocardial Ischemia, and Risk for Sudden Death," *Circulation Research*, vol. 69, No. 5, Nov. 1991 (pp. 1389-1401).

Ziad F. Issa et al., "Thoracic Spinal Cord Stimulation Reduces the Risk of Ischemic Ventricular Arrhythmias in a Postinfarction Heart Failure Canine Model," *Circulation Journal of the American Heart Association*, 2005;111:3217-3220.

Robert D. Foreman et al., "Modulation of intrinsic cardiac neurons by spinal cord stimulation: implications for its therapeutic use in angina pectoris," *Cardiovascular Research*, 47 (2000) 367-375.

Masahiro Ogawa, MD et al., "Left Stellate Ganglion and Vagal Nerve Activity and Cardiac Arrhthmias in Ambulatory Dogs With Pacing-Induced Congestive Heart Failure," *Journal of the American College of Cardiology*, vol. 50, No. 4 (2007) (9 pages).

Xiao-Jun Du et al., "Role of sympathoadrenergic mechanisms in arrhythmogenesis," *Cardiovascular Research*, 43 (1999) 832-834.

Federico Lombardi et al., "Sudden cardiac death: role of heart rate variability to identify patients at risk," *Cardiovascular Research*, 50 (2001) 210-217.

Peter J. Schwartz et al., "Long term vagal stimulation in patients with advanced heart failure First experience in man," *European Journal of Heart Failure*, (2008) 8 pages.

Shengmei Zhou et al., "Spontaneous stellate ganglion nerve activity and ventricular arrhythmia in a canine model of sudden death," *Heart Rhythm*, vol. 5, No. 1 (Jan. 2008) pp. 131-139.

"Heart Rate Variability Scientific Background . . . ," http://www.heartsmartlive.com/science.htm, last printed Oct. 21, 2008 (6 pages).

Ronald D. Janes et al., "Anatomy of Human Extrinsic Cardiac Nerves and Ganglia," *The American Journal of Cardiology*, vol. 57 (Feb. 1, 1986) pp. 299-309.

Marco Bettoni, MD et al., "Autonomic Tone Variations Before the Onset of Paroxysmal Atrial Fibrillation," *Circulation*, vol. 105 (2002) pp. 2753-2759.

Gerald F. DiBona, "Neurogenic regulation of renal tubular sodium reabsorption," *Am. J. Physiol.*, 233(2): F73-F81 (1977).

U.S. Appl. No. 12/263,202, filed Oct. 31, 2008 by Venkatesh Manda et al. entitled Electrical Renal Autonomic Blockade.

\* cited by examiner

LEGEND

CERVICAL SYMPATHETIC TRUNK – 11

SUBCLAVIAN ANSEA NERVE – 13

SUBCLAVIAN ARTERY – 8

MIDDLE CERVICAL GANGLIA – 15

CARDIOPULMONARY NERVES – 16

MEDIASTINAL GANGLION – 18

STELLATE GANGLION – 19

LEAD – 52

BASKET ELECTRODE – 54

LEAD – 62

STENT ELECTRODE – 64

SUBCLAVIAN ANSAE STIMULATION

TECHNICAL FIELD

The invention relates to techniques for improving cardiac performance.

BACKGROUND

Sudden cardiac arrest (SCA) is one of the most critical medical problems in the world today. In the United States alone, SCA results in the death of over 325,000 people each year. Most sudden cardiac deaths are caused by ventricular arrhythmias like ventricular tachycardia (VT) and ventricular fibrillation (VF).

Angina pectoris, i.e., chest pain commonly referred to as angina, may occur during ischemia such as acute myocardial infarction, i.e., a heart attack, which is generally caused by occlusion of a coronary artery. Angina can also occur for other reasons including coronary vasospasm, a condition when coronary blood vessels spasm, leading to vasoconstriction. Coronary vasospasm is not necessarily life-threatening, but may be in some instances as coronary vasospasm can result in ischemia and even myocardial infarction. Coronary vasospasm may occur adjacent to a fixed stenosis, which can increase the likelihood of ischemia.

SUMMARY

In general, the disclosure describes techniques for improving cardiac performance by applying stimulation to the subclavian ansae nerve. Stimulation of the subclavian ansae nerve may be used to block or limit sympathetic nervous system signals. For example, stimulation of the subclavian ansae nerve may inhibit the sympathetic nervous system in a patient to reduce incidence of ventricular arrhythmias like VT and VF, such as VT and VF caused by ischemia-induced activation of cardiac neurons. By reducing the occurrence of ventricular arrhythmias, stimulation of the subclavian ansae nerve can reduce the likelihood of sudden cardiac death in a patient.

Stimulation of the subclavian ansae nerve may also partially or entirely alleviate coronary vasospasm. Patients experiencing angina due to coronary vasospasm may experience relief from stimulation therapy of the subclavian ansae nerve. Because it may be difficult or impossible to quickly determine the cause of angina in a patient, treatment of a patient experiencing angina may include stimulation therapy directed to the subclavian ansae nerve to relieve coronary vasospasm in addition to common emergency treatments for myocardial infarction due to coronary artery occlusion.

One example is directed to a method comprising identifying a human patient as having a cardiac condition, and delivering stimulation therapy to a subclavian ansae nerve of a human patient with a stimulation electrode.

Another example is directed to a method comprising determining a human patient is experiencing angina pectoris; and stimulating a subclavian ansae nerve in the patient in response to the determination.

A different example is directed to a medical system comprising a set of one or more electrodes, a stimulation generator coupled to the electrodes, and a processor configured to control the stimulation generator to generate a stimulation therapy signal configured to at least partially block neural activity in a subclavian ansae nerve in a patient, and deliver the stimulation therapy signal via the set of electrodes.

Another example is directed to a medical device comprising means for generating a stimulation therapy signal configured to at least partially block neural activity in a subclavian ansae nerve, and means for delivering the stimulation therapy signal to the subclavian ansae nerve in a patient.

The details of one or more examples of the invention are set forth in the accompanying drawings and the description below. Other features, objects, and advantages of the invention will be apparent from the description and drawings, and from the claims.

DETAILED DESCRIPTION

Figure 1:
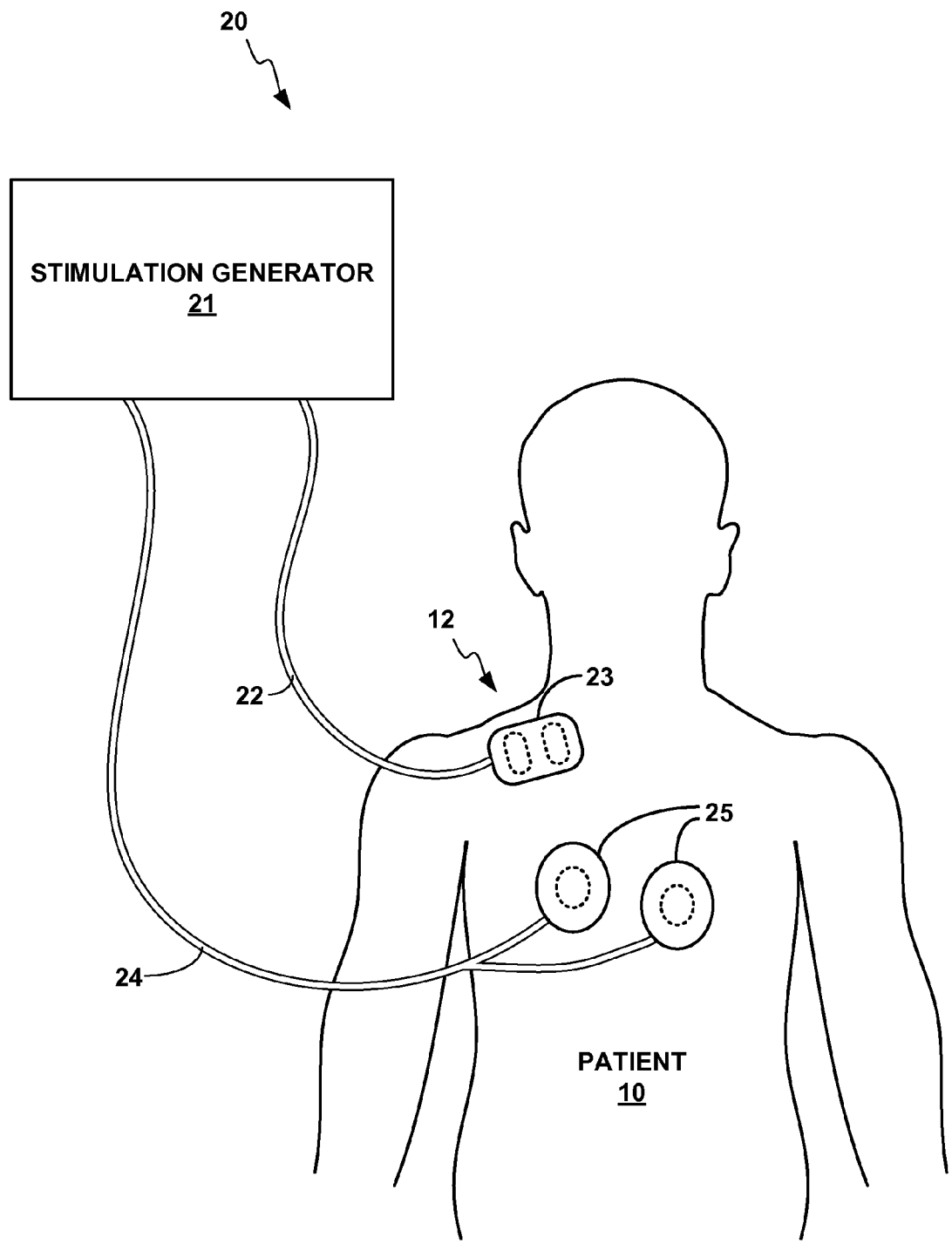
FIG. 1 is a conceptual illustration of an example transcutaneous stimulation system for delivering stimulation therapy to a subclavian ansae nerve of a patient.

Excitation of the sympathetic nervous system can result in an increased propensity for VT and VF and trigger sudden cardiac death. Spinal cord stimulation (SCS) can suppress activity generated by cardiac neurons, particularly ischemia-induced activation of cardiac neurons by inhibiting the sympathetic nervous system. For example, electrical activation of the dorsal columns at the T1-T2 spinal segments significantly reduces activity generated by intrinsic cardiac neurons in their basal conditions, as well as when activated in the presence of regional ventricular ischemia.

Canine testing has demonstrated that the suppressor effect of SCS on intrinsic cardiac neural activity is reduced or eliminated when the subclavian ansae is transected. This indicates that reduced activity in intrinsic cardiac neurons is due primarily to the influence of spinal cord neurons acting via the sympathetic nervous system. SCS induces inhibition of impulses in the small-diameter fiber systems in the spinal cord and therefore reduces sympathetic outflow to the heart. Thus, blocking stimulation of the subclavian ansae can also reduce sympathetic outflow to the heart.

Inhibiting the sympathetic nervous system can, for example, reduce incidence of ventricular arrhythmias like VT and VF during ischemia, thereby reducing the likelihood of sudden cardiac death in a patient. In addition, blocking stimulation of the subclavian ansae can also mitigate coronary vasospasm by reducing sympathetic outflow. Inhibition of the sympathetic nervous system may have other uses as well.

As compared to SCS, blocking sympathetic nervous system signals via the subclavian ansae may provide one or more of the following advantages. For example, implanted material or objects can, in rare cases, be associated within infection at the site of implantation within a patient. For example, infection may occur in patents approximately 2 percent of time with a SCS implant procedure. An infection near the subclavian ansae would generally be less problematic than an infection in the spine of a patient. Another potential advantage is that stimulation therapy directed towards the subclavian ansae may result in a lower occurrence of side-effects than with SCS. One side effect of SCS can be involuntary diaphragm contractions, i.e., hiccups. Stimulation of the subclavian ansae can result in lower occurrence of side-effects because there are less nerves adjacent to the subclavian ansae than there are in the spinal cord of a patient, and less physiological functionality associated with the subclavian ansae than with the spinal cord. The relatively isolated location and limited functionality of the subclavian ansae may also allow for higher stimulation magnitudes than practical with SCS, which could have a positive effect on the efficacy of the treatment. In addition, stimulation of the subclavian ansea can be accomplished transcutaneously, without any implantation. This substantially eliminates the risk of infection and also allows for emergency stimulation treatment, e.g., in an ambulance.

In general, the disclosure describes techniques for improving cardiac performance by applying stimulation to the subclavian ansae nerve. While the examples shown in the figures include leads coupled at their proximal ends to a stimulation therapy controller, e.g., implantable medical device (IMD), located remotely from the electrodes, other configurations are also possible and contemplated. In some examples, electrodes are formed on a portion of a housing, or carried by a member coupled to a housing, of stimulation generator located proximate to or at the stimulation site, e.g., a microstimulator. In other examples, a member or device comprising electrodes is located at stimulation site and is wirelessly coupled to an implanted or external stimulation controller or generator.

FIG. 1 is a conceptual diagram illustrating an example stimulation system 20 comprising a stimulation generator 21 and transcutaneous medical leads 22, 24. Medical leads 22, 24 each include at least two transcutaneous electrodes. System 20 is capable of delivering stimulation therapy to the subclavian ansae nerve of patient 10, and also capable of delivering cardiac electrical stimulation therapy, such as pacing pulses or defibrillation shocks, to patient 10. In the example shown in FIG. 1, medical lead 22 is configured to deliver stimulation therapy to area 12, which is proximate to the subclavian ansae nerve of patient 10, and thereby deliver stimulation therapy to the subclavian ansae. Medical lead 24 is configured to deliver cardiac stimulation therapy to patient 10 and/or sense one or more physiological parameters of patient 10.

Delivering stimulation therapy to area 12 with electrodes 23 of lead 22 may block or limit sympathetic nervous system signals traversing the subclavian ansae nerve of patient 10. High-frequency biphasic waveform signals are suitable for blocking transmission of neurological signals on the subclavian ansae nerve. This may suppress sympathetic nervous system symptoms and mitigate coronary vasospasm.

Patients experiencing angina due to coronary vasospasm may experience relief from stimulation therapy of the subclavian ansae nerve. Because it may be difficult or impossible to quickly determine the cause of angina in a patient, treatment of a patient experiencing angina, such as patient 10, may include stimulation therapy directed to the subclavian ansae nerve to relieve coronary vasospasm in addition to common emergency treatments for myocardial infarction due to coronary artery occlusion. Administering treatment for both coronary vasospasm and coronary artery occlusion increases the chances that the treatment will mitigate the cause of the angina.

In addition, stimulation of the of the subclavian ansae nerve may also be used to treat a patient experiencing myocardial infarction. For example, stimulation of the subclavian ansae nerve may mitigate reperfusion damage in a myocardial infarction patient by slowing the rate of reperfusion following ischemia. As another example, stimulation of the subclavian ansae nerve in a myocardial infarction patient may reduce the probability of ischemia-induced arrhythmias in the patient. For these reasons, it may be suitable to apply stimulation to area 12 even if it is known that patient 10 is experiencing myocardial infarction and not coronary vasospasm.

Electrodes 25 may be used to deliver cardiac stimulation therapy to patient 10, e.g., if patient 10 is experiencing sudden cardiac arrest. For example, stimulation generator 21 may include the capabilities of an automated external defibrillator (AED). As such, stimulation generator 21 may automatically diagnose an electrocardiogram (ECG) from patient 10. Alternatively, stimulation generator 21 may require more human intervention than an AED or fully automatic defibrillator.

Stimulation generator 21 is configured to determine an appropriate electrical stimulation therapy, and then generate a charge that is delivered to the patient 10 as the pacing stimulus or defibrillation shock with one or more of electrodes 25. One or more of electrodes 23, 25 may also be configured to sense one or more physiological and/or physical parameters of the patient 22 and supply signals representative of these parameters to stimulation generator 21. Stimulation generator 21 may additionally include or be coupled to, e.g., wirelessly or by one or more leads, one or more other external or implanted sensors to sense the physiological and/or physical parameters (not shown in FIG. 1). The other sensors may include, as examples, additional electrodes, accelerometers, strain gauges, chemical sensors, optical sensors, ultrasonic sensors, capacitive pressure sensors, or the like. In some examples, stimulation generator 21 may communicate with an implantable medical device (IMD, not shown in FIG. 1) within the patient that includes such sensors.

The one or more physiological and/or physical parameters of the patient can include information about the patient's heart, blood, temperature and/or the like. More particularly, the sensed physical parameters may include sympathetic tone, parasympathetic tone, electrocardiogram (ECG) data, heart rhythm data, heart rate data, heart rate regularity data, cardiac output data, blood pressure data, blood flow data, blood oxygen saturation data, a patient's level of perfusion, respiration data and/or any other physiological parameter that is used in the art to assess the physical condition of a patient.

The signals provided by one or more of electrodes 23, 25, or another sensor, are preferably evaluated by stimulation generator 21 to determine, among other things, whether ansae blocking stimulation, a defibrillation shock, cardioversion shock or pacing stimuli should be applied to patient 10. Stimulation generator 21 can also evaluate the signals provided by one or more of electrodes 23, 25 and/or one or more other sensors to determine the effectiveness of applied blocking stimulation. Stimulation generator 21 may also evaluate the signals provided by one or more of electrodes 23, 25 and/or one or more other sensors to determine waveform parameters for ansae blocking stimulation, such voltage or current amplitude, energy, rate or frequency, pulse width (in the case of stimulation delivered in the form of pulses, and/or duration or duty cycle, magnitude and duration of the defibrillation shock, as well as the waveform parameters for pacing stimuli.

Figure 2A:
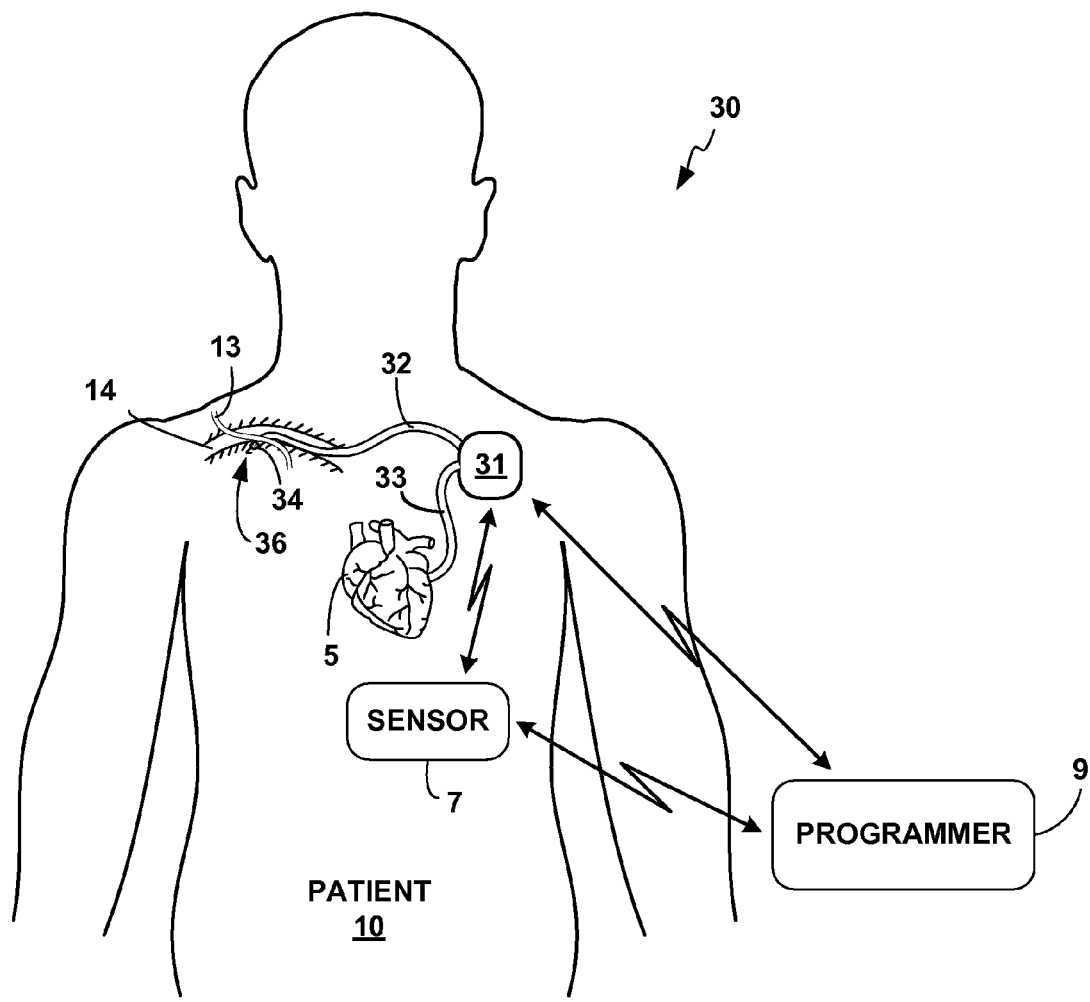
FIG. 2A is a conceptual illustration of an example implantable stimulation system for delivering stimulation therapy to a subclavian ansae nerve of a patient.
Figure 2B:
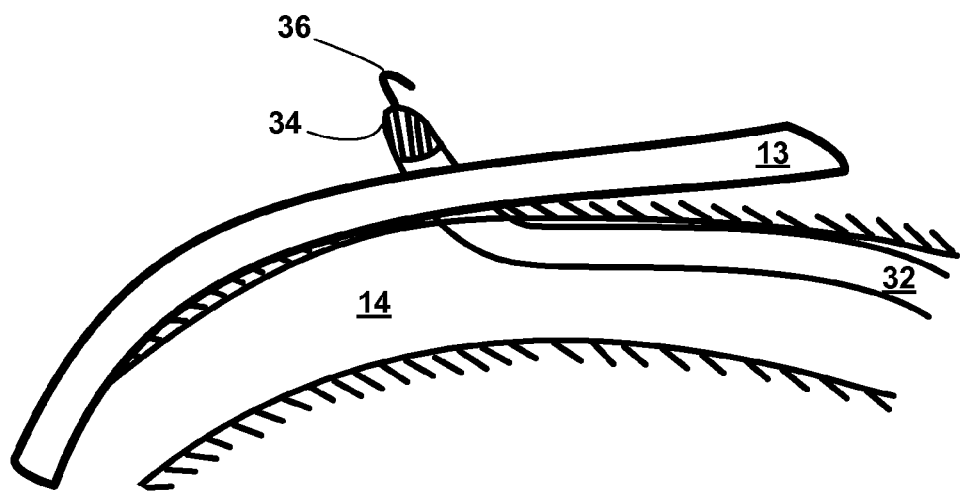
FIG. 2B is a close-up view of the distal end of an implantable stimulation lead in the implantable stimulation system of FIG. 2A.

FIG. 2A is a conceptual illustration of another example implantable stimulation system 30 for delivering stimulation therapy to a subclavian ansae nerve of a patient. FIG. 2B is a close-up view of the distal end of a stimulation lead 32 in system 30. System 30 comprises an implantable medical device (IMD) 31, and implantable medical leads 32, 33 electrically coupled to IMD 31. In the example shown in FIG. 2A, IMD 31 is implanted within a patient 10 to deliver electrical stimulation therapy to subclavian ansae nerve 13 of patient 10. IMD 31 includes a neurostimulation module that generates a blocking signal applied subclavian ansae nerve 13 via lead 32 and electrode 34. IMD 31 also delivers cardiac stimulation therapy to heart 5 via lead 33. For example, IMD 31 may be configured to deliver one or more of pacing, cardioversion and defibrillation.

In some examples, IMD 31 delivers a high frequency, biphasic stimulation signal to subclavian ansae 13 to decrease sympathetic activity via lead 32 and electrode 34. For example, IMD 31 may generate a stimulation signal with a frequency of about 100 hertz to about 20 kilohertz and deliver the stimulation signal to subclavian ansae 13 of patient 10. In some examples, the stimulation signal may have a frequency of about 100 hertz to about 10 kilohertz. In other examples, IMD 31 may generate a stimulation signal with a frequency of about 2 kilohertz or higher. The stimulation signal may have a voltage amplitude of about 0.5 volts to about 20 volts and, in some examples, a voltage amplitude of about 0.5 volts to about 10 volts. Alternatively, the stimulation signal may have a current amplitude of about 1 to about 12 milliamperes. A biphasic stimulation signal has portions with opposite polarities, e.g., positive and negative portions.

High-frequency biphasic electrical stimulation may create a reversible functional conduction block in subclavian ansae 13. Biphasic electrical stimulation may also be charge-balanced, and thereby prevent and/or reduce corrosion of electrodes of lead 32.

IMD 31 may use alternating current (AC) to deliver stimulation signals to reduce sympathetic activity. High-frequency AC stimulation has been shown to produce block of nerve conduction in motor nerves and may also be effective at producing conduction block in subclavian ansae 13. IMD 31 may also use monopolar and/or multipolar electrode configurations to achieve at least partial conduction block in subclavian ansae 13. Example stimulation waveforms that IMD 31 may utilize to achieve at least partial nerve blockage include sinusoidal waveforms, square waveforms, and other continuous time signals. As an alternative, IMD 31 may deliver stimulation in the form of pulses.

In some examples, IMD 31 delivers high voltage stimulation in addition to or as an alternative to high frequency stimulation. High voltage stimulation may use voltages significantly higher than the physiological voltages subclavian ansae 13 use to conduct neural signals. High voltage stimulation may stun subclavian ansae 13 and at least partially prevent subclavian ansae 13 from conducting neural signals. High voltage stimulation may utilize direct current (DC) signals and may be configured to minimize damage to subclavian ansae 13.

Lead 32 is configured for intravascular, e.g., intravenous, introduction. For example, lead 32 may have a lead body diameter of between 0.020 inches and 0.100 inches. In the illustrated example, a portion of lead 32 is within subclavian vein 14 of patient 10. In other examples, lead 32 may alternatively be positioned within the subclavian artery to deliver stimulation to subclavian ansae nerve 13.

The distal end of lead 32, which includes electrode 34, passes through a transvascular lumen in subclavian vein 14 to an extravascular location adjacent to subclavian ansae nerve 13. Lead 32 also includes fixation element 36 to secure electrode 34 within patient 10. Fixation element 36 provides a hooked configuration; any other suitable fixation elements and techniques including sutures, tines and barb fixation elements may also be used. Lead 32 includes only one tip electrode 34, e.g., for unipolar delivery of stimulation, but other electrode configurations are also possible. For example, one alternative is lead 42 (FIG. 3), which includes two ring electrodes, e.g., for bipolar stimulation.

Leads including the features described herein may be used to deliver neurostimulation therapy from a medical device to target neural tissues of a patient, such as the subclavian ansae nerve. Furthermore, although described herein as being coupled to IMDs, implantable medical leads may also be percutaneously coupled to an external medical device for delivery of electrical stimulation to target locations within a patient.

System 30 including IMD 31 and lead 33 also serves as a cardiac pacemaker, cardioverter, defibrillator, or pacemaker-cardioverter-defibrillator (PCD) that generates therapeutic electrical stimulation for pacing, cardioversion or defibrillation, which may take the form of pulses or continuous time signals. While only lead 33 is shown as going to heart 5, other examples may include multiple leads for cardiac stimulation.

In some examples, at least one of the electrodes of lead 32, or one or more different leads, may include at least one sense electrode or sensor that senses a physiological parameter of patient 10, such as, but not limited to, sympathetic tone, parasympathetic tone, electrocardiogram (ECG) parameters, a heart rate, QRS width, atrioventricular (AV) Dissociation, respiration rate, respiratory volume, core temperature, skeletal muscle activity, blood oxygen level, cardiac output, blood pressure, intracardiac pressure, time derivative of intracardiac pressure (dP/dt), electromyogram (EMG) parameters, or electroencephalogram (EEG) parameters. Sense electrodes may be the same electrodes used for delivery of electrical stimulation to patient 10, or different electrodes. Electrodes on leads 32, 33 may also function as sensing electrodes, e.g., to measure cardiac performance, heart rate or other physiological data. Additional leads may also be used to measure physiological information. For example, a combination of electrodes may be used to measure thoracic impedance to evaluate respiration.

Therapy system 10 may also include at least one sensor 7 in addition to or instead of sense electrodes and sensors on the leads. Sensor 7 may be configured to detect an activity level, motion, posture, intracardiac, intravascular or other pressure within the patient, or another physiological parameter of patient 10. For example, sensor 7 may comprise an accelerometer. Sensor 7 may generate a signal that varies as a function of at least one physiological parameter of patient 10.

Sensor 7 may be implanted within or external to patient 10, and may be wirelessly coupled to IMD 31 or coupled to IMD 31 via a lead, such as leads 32 or another lead. For example, sensor 7 may be implanted within patient 10 at a different site than IMD 31 or sensor 7 may be external. In some examples, sensor 7 may be located on or within a housing of IMD 31. In addition or instead of being coupled to IMD 31, in some cases, sensor 7 may be wirelessly coupled to programmer 9 or coupled to programmer 9 by a wired connection. As used herein, the term "sensor" refers to at least one electrode, or any other sensor, that provides a signal that varies as a function of a sensed physiological parameter.

The sensed physiological parameters may be used to determine the occurrence of ventricular arrhythmias like VT and VF or coronary vasospasm in patient 10. As another example, the sensed physiological parameters may be used to determine an autonomic imbalance of the sympathetic and parasympathetic nervous systems, a sympathetic tone and/or a parasympathetic tone of patient 10. In response to the determination of ventricular arrhythmias, coronary vasospasm or autonomic imbalance, IMD 31 may generate blocking stimulation signals, such as high-frequency biphasic waveform signals, to disrupt sympathetic nervous system signals in subclavian ansae nerve 13. In some examples, may start, stop or otherwise modify the stimulation based on the signal, e.g., responsive and/or closed loop.

One technique for characterizing the autonomic balance of patient 10 includes evaluation of the High-frequency (HF) and Low Frequency (LF) neurological signals. The LF/HF ratio can indicate balance between sympathetic and parasympathetic tone. A decrease in the LF/HF ratio might indicate either increase in parasympathetic or decrease in sympathetic tone. A LF/HF ratio should be considered together with absolute values of both LF and HF to determine what factor contributes to an autonomic disbalance. Techniques for evaluation of the LF/HF ratio include analyzing heart rate intervals or systolic blood pressure intervals. Neurological signals may also be directly evaluated by considering the amplitude of the rectified signal in the direction of the heart.

Generally, the HF power spectrum is evaluated in the range from 0.15 to 0.4 Hz. This band reflects parasympathetic (vagal) tone and fluctuations caused by spontaneous respiration known as respiratory sinus arrhythmia. In addition, the LF power spectrum is evaluated in the range from 0.04 to 0.15 Hz. This band can reflect both sympathetic and parasympathetic tone. IMD 31 may include a sensor electrode to detect parasympathetic tone at the vagus nerve of patient 10 and another sensor electrode to detect sympathetic tone at the stellate ganglion of patient 10. As another example, IMD 31 may detect sympathetic tone in subclavian ansae nerve 13 using electrode 36.

In addition, IMD 31 may also generate blocking stimulation signals directed towards subclavian ansae nerve 13 according to a preprogrammed sequence, e.g., at regularly scheduled intervals. Blocking stimulation of the subclavian ansae nerve may inhibit the sympathetic nervous system in a patient to reduce incidence of ventricular arrhythmias like VT and VF, even after the blocking stimulation has occurred. In this manner, it is not necessary for IMD 31 to generate a continuous blocking stimulation signal to reduce the risk of sudden cardiac arrest in patient 10.

As shown in FIG. 2A, system 30 may also include a programmer 9, which may be a handheld device, portable computer, or workstation that provides a user interface to a clinician or other user. The clinician may interact with the user interface to program stimulation parameters for IMD 31, which may include, for example, the electrodes of leads that are activated, the polarity of each of the activated electrodes, a current or voltage amplitude for each of the activated electrodes and, in the case of stimulation in the form of electrical pulses, pulse width and pulse rate (or frequency) for stimulation signals to be delivered to patient 10. As referred to herein, an amplitude of stimulation therapy may be characterized as a magnitude of a time varying waveform. For example, an amplitude of stimulation therapy may be measured in terms of voltage (volts), current (ampere), or electric field (volts/meter). Typically, amplitude is expressed in terms of a peak, peak to peak, or root mean squared (rms) value. The clinician may also interact with the user interface to program escape intervals, rate response parameters, or any other stimulation parameters known for use in controlling cardiac pacing, or other types of therapeutic stimulation.

Programmer 9 supports telemetry (e.g., radio frequency telemetry) with IMD 31 to download stimulation parameters and, optionally, upload operational or physiological data stored by IMD 31. In this manner, the clinician may periodically interrogate IMD 31 to evaluate efficacy and, if necessary, modify the stimulation parameters. IMD 31 and programmer 9 may communicate via cables or a wireless communication, as shown in FIG. 2A. Programmer 9 may, for example, communicate via wireless communication with IMD 31 using RF telemetry techniques known in the art.

Figure 3:
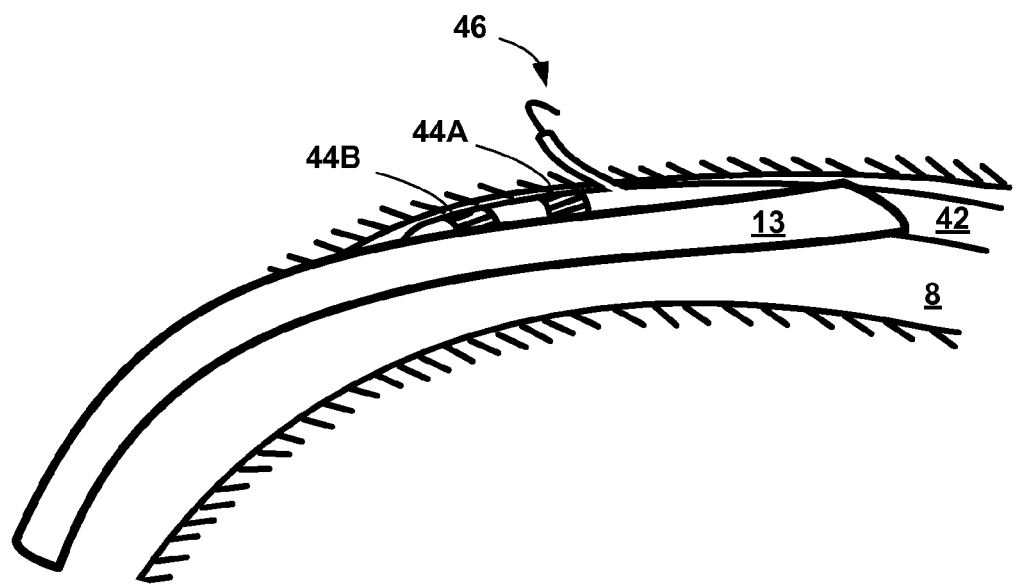
FIG. 3 is a conceptual illustration of the distal end of another example implantable stimulation lead including an alternative electrode configuration and fixation element as compared to the stimulation lead of the implantable stimulation system of FIGS. 2A-2B.

FIG. 3 is a conceptual illustration of the distal end of stimulation lead 42. Lead 42 may be used in conjunction with IMD 31 and other components of system 30 (FIG. 2A). Lead 42 includes ring electrodes 44A and 44B (collectively "electrodes 44") and an alternative electrode configuration and fixation element as compared to stimulation lead 32 (FIGS. 2A-2B). In this manner, stimulation lead 42 provides an alternative to stimulation lead 32 (FIGS. 2A-2B).

Lead 42 is configured for intravenous introduction. For example, lead 42 may have a lead body diameter of between 0.020 inches and 0.100 inches. The distal end of lead 42 is contained within subclavian artery 8 of a patient. Electrodes 44 are positioned to deliver stimulation therapy to subclavian ansae nerve 13 transvascularly, e.g., through the arterial wall. In other examples, lead 42 and electrodes 44 may be positioned within the subclavian vein to deliver stimulation to subclavian ansae nerve 13. Lead 42 also includes fixation element 46 to secure electrodes 44 within subclavian artery 8 adjacent to subclavian ansae nerve 13. Fixation element 46 is located adjacent to the distal end of lead 42 and provides a hooked configuration; any other suitable fixation elements and techniques including sutures, tines and barb fixation elements may also be used.

Stimulation therapy to subclavian ansae nerve 13 may be applied using one or both of electrodes 44. For example, electrode 44A may be configured as a cathode while electrode 44B is simultaneously configured as an anode. Alternatively, one or both of electrodes 44 may be configured as cathodes while the housing of IMD 31 simultaneously serves as an anode. During high-frequency bipolar stimulation signals, such as those useful for blocking neurological signals in subclavian ansae nerve 13, the polarities of electrodes 44 and the housing of IMD 31 will invert repeatedly during the stimulation. The actual electrode combination and other stimulation parameters may be selected by a clinician after implantation, e.g., using programmer 9 (FIG. 2A).

Figure 4:
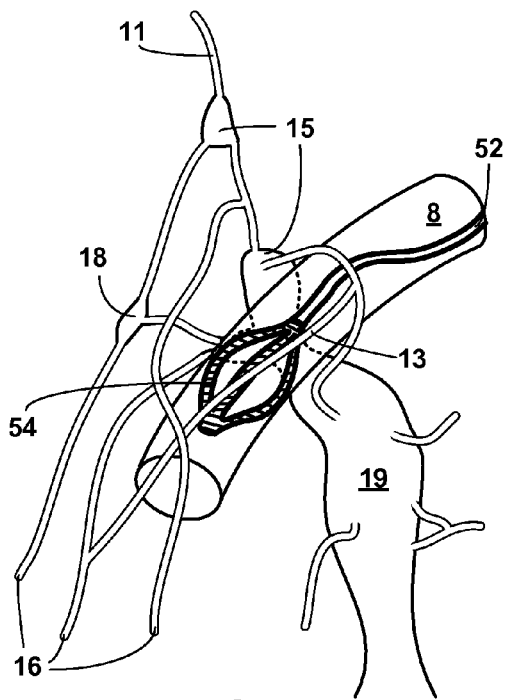
FIG. 4 is a conceptual illustration of the distal end of another example implantable stimulation lead including a basket-like transvascular electrode for delivering stimulation therapy to a subclavian ansae nerve of a patient.
Figure 5:
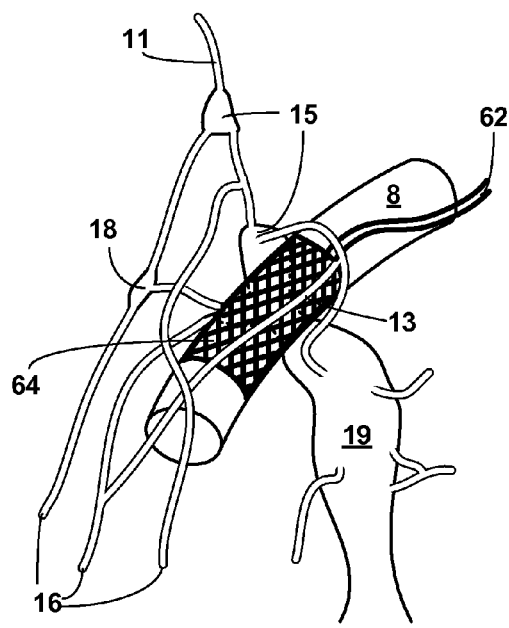
FIG. 5 is a conceptual illustration of the distal end of another example implantable stimulation lead including a stent-like transvascular electrode for delivering stimulation therapy to a subclavian ansae nerve of a patient.

FIG. 4 is a conceptual illustration of the distal end of implantable stimulation lead 52 including a basket-like transvascular electrode 54 for delivering stimulation therapy to subclavian ansae nerve 13. FIG. 5 is a conceptual illustration of the distal end of implantable stimulation lead 62 including a stent-like transvascular electrode 64 for delivering stimulation therapy to subclavian ansae nerve 13. Leads 52 and 62 provide alternatives to leads 32 and 42 (FIGS. 2A, 2B and 3) and may be used in conjunction with IMD 31 and other components of system 30 (FIG. 2A). FIGS. 4 and 5 show the nervous system of a patient adjacent subclavian ansae nerve 13 in greater detail than that shown in FIGS. 2A, 2B and 3.

The nervous system details shown in FIGS. 4 and 5 are merely representative and can be different in different patients. For this reason, FIGS. 4 and 5 and the following description should be considered only as one example of neuron structures in a patient. As shown in FIGS. 4-5, cervical sympathetic trunk 11 leads to a middle cervical ganglion 15. The middle cervical ganglia 15 connect to cardiopulmonary nerves 16 as well as to stellate ganglion 19. As previously mentioned, stellate ganglion 19 is one location that the sympathetic tone of a patient can be detected using a sensing electrode. In some instances, a mediastinal ganglion serves as a junction between cervical sympathetic trunk 11, stellate ganglion 19 and a cardiopulmonary nerve 16. Subclavian ansae nerve 13 runs adjacent to subclavian artery 8 between a cardiopulmonary nerve 16 and a neuron connection between cervical sympathetic trunk 11 and stellate ganglion 19.

Because of the location of subclavian ansae nerve 13 is adjacent to subclavian artery 8 at the position shown in FIGS. 4-5, transvascular electrodes may be suitable to deliver stimulation therapy to subclavian ansae nerve 13 from within subclavian artery 8. As shown in FIG. 4, one example of a suitable transvascular electrode is basket-like electrode 54. Basket-like electrode 54 includes discrete elements forming a hollow frame that contacts the interior surfaces of a vascular structure. In some examples, basket-like electrode 54 may be located in position within subclavian artery 8 in a compressed state and then released to contact the interior surfaces of subclavian artery 8 adjacent to subclavian ansae nerve 13. As one example, basket-like electrode 54 may comprise a shape-memory alloy such as nitinol.

In other examples, an electrode structure in a basket-like configuration may include more than one discrete electrode. For example, an electrode structure in a basket-like configuration may include selectable electrode segments such that a direction of a stimulation field can be biased towards subclavian ansae nerve 13. In addition, an electrode structure in a basket-like configuration may include an electrode pair to provide both an anode and a cathode adjacent to subclavian ansae nerve 13 simultaneously. In addition, lead 52 may also include an electrode in addition to basket-like electrode 54. For example, the addition electrode could be a ring electrode. Other configurations of lead 52 are also possible.

FIG. 5 illustrates the distal end of lead 62, which includes another example of a suitable transvascular electrode, stent-like electrode 64. Stent-like electrode 64 includes a wire metal mesh. Stent-like electrode 64 may be located in position within subclavian artery 8 in a compressed state and then expanded to contact the interior surfaces of subclavian artery 8 adjacent to subclavian ansae nerve 13. As one example, stent-like electrode 64 may be expanded using a balloon catheter, as is common for deployment of stents used during angioplasty.

In other examples, an electrode structure in a stent-like configuration may include more than one discrete electrode. For example, an electrode structure in a stent-like configuration may include selectable electrode segments such that a direction of a stimulation field can be manipulated to increase its intersection with subclavian ansae nerve 13. In addition, an electrode structure in a stent-like configuration may include an electrode pair to provide both an anode and a cathode adjacent to subclavian ansae nerve 13 simultaneously. One configuration of an electrode pair includes two circular wire mesh electrodes connected via a non-conductive strip. In addition, lead 62 may also include an electrode in addition to stent-like electrode 64. For example, the additional electrode could be a ring electrode. Other configurations of lead 62 are also possible.

Additional electrode configuration, including transvascular electrode configurations may also be suitable for stimulation of a subclavian ansea nerve in a patient. For example, electrode configurations, including transvascular electrode configurations, are described in U.S. Pat. No. 7,191,015, issued on Mar. 13, 2007, titled "DEVICES AND METHODS FOR TRANSLUMINAL OR TRANSTHORACIC INTERSTITIAL ELECTRODE PLACEMENT" to Lamson et al., the entire contents of which are incorporated by reference herein.

Figure 6:
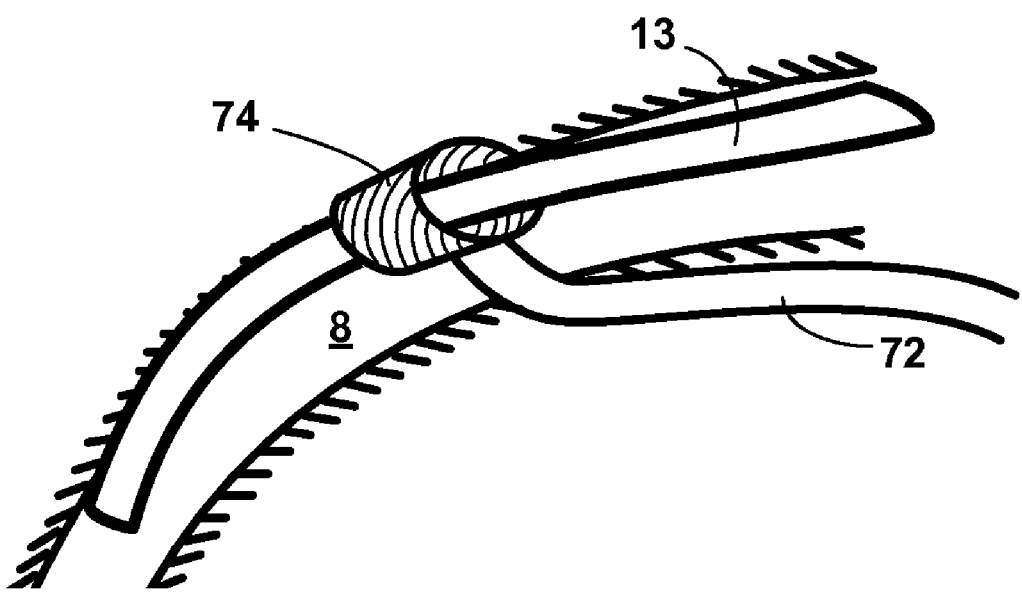
FIG. 6 is a conceptual illustration of the distal end of another example implantable stimulation lead including a nerve-cuff electrode for delivering stimulation therapy to a subclavian ansae nerve of a patient.

FIG. 6 is a conceptual illustration of the distal end of stimulation lead 72. Lead 72 may be used in conjunction with IMD 31 and other components of system 30 (FIG. 2A). Lead 72 includes nerve cuff electrode 74 and provides an alternative to stimulation leads 32, 42, 52 and 62 (FIGS. 2A-5).

In contrast to stimulation leads 32, 42, 52 and 62, lead 72 is not located within a vascular structure. This may simplify the placement of lead 72 and also facilitate a more confined stimulation field than with leads 32, 42, 52 and 62. However, implantation of lead 72 may cause more trauma to a patient than implantation of a lead via a vascular structure.

Stimulation therapy to subclavian ansae nerve 13 may be applied using nerve cuff electrode 74. Unipolar stimulation may be supplied using the housing of an IMD with cuff electrode 74. Alternatively, lead 72 may also include an electrode in addition to nerve cuff electrode 74, such as a ring electrode, or a cuff may include a plurality of discrete electrodes. Furthermore, although illustrated with cuff electrode 74 around only ansae nerve 13 in FIG. 6, in other examples, a cuff may be disposed around both subclavian artery 8 and ansae nerve 13. Alternatively, a cuff electrode assembly may include a U-shaped cross section configured to fit about a selected portion of the circumference of a nerve, e.g., subclavian ansae nerve 13, or vessel, e.g., subclavian artery 8. Examples of cuff electrode assemblies are described in U.S. Pat. No. 5,344,438 to Testerman et al., which issued on Sep. 4, 1994 and is entitled, "CUFF ELECTRODE," the entire contents of which are incorporated by reference herein.

Figure 7:
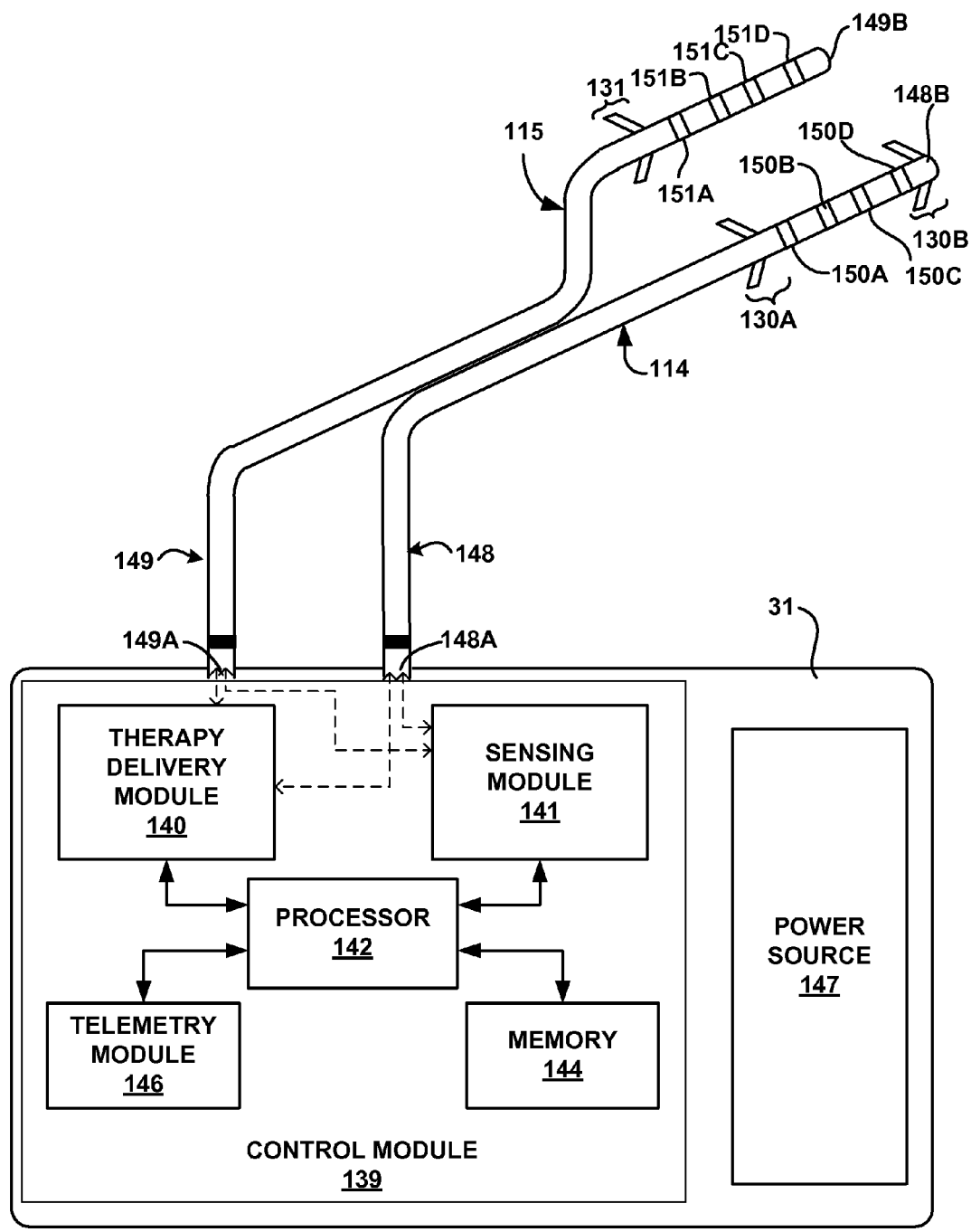
FIG. 7 is a block diagram illustrating various components of an electrical stimulator and medical leads of a stimulation therapy delivery system.

FIG. 7 is a block diagram illustrating a general example of various components of electrical stimulator 31 and medical leads 114, 115. For example, electrical stimulator 31 may be similar to electrical stimulator 31 in FIG. 2. We should note that the device of FIG. 1 may include similar components. However, in contrast to lead 34 (FIG. 2), medical leads 114, 115 include multiple ring electrodes instead of a single distal electrode. In addition, while medical leads 114, 115 are implantable, the functionality of electrical stimulator 31 itself may be similar to the functionality of external stimulation generator 21 (FIG. 1). These are just examples of implantable medical leads that may be used to deliver stimulation therapy proximate the subclavian ansae nerve of a patient. As previously mentioned, medical leads with other electrode configurations may also be used.

At least one of medical leads 114, 115 is implanted proximate the subclavian ansae nerve of a patient. One of medical leads 114, 115 may be implanted to provide stimulation therapy to a different region of a patient. For example, one of medical leads 114, 115 may be implanted to deliver stimulation therapy proximate the vagus nerve of a patient or to deliver cardiac stimulation, e.g., pacing therapy or defibrillation therapy.

One or both of medical leads 114, 115 may also be used for patient sensing and, in some cases, for both sensing and stimulation. As shown in FIG. 7, leads 114, 115 are in electrical communication with both therapy delivery module 140 and sensing module 141. For example, electrodes on implantable medical leads may detect electrical signals within a patient, such as a cardiac electrogram, or be used to measure impedance within a patient, in addition to delivering electrical stimulation.

Sensing module 141 detects physiological parameters via leads 114, 115. In addition, sensing module 141 may also sense data from one or more additional sensors (not shown in FIG. 7) via a wired or wireless connection. Sensing data may include, but not is limited to, sympathetic tone, parasympathetic tone, electrocardiogram (ECG) parameters, a heart rate, QRS width, atrioventricular (AV) Dissociation, respiration rate, respiratory volume, core temperature, skeletal muscle activity, blood oxygen level, cardiac output, blood pressure, intracardiac pressure, time derivative of intracardiac pressure (dP/dt), electromyogram (EMG) parameters, or electroencephalogram (EEG) parameters.

Electrical stimulator 31 may include power source 147 and control module 139 including therapy delivery module 140, processor 142, memory 144 and telemetry module 146. As one example, all or a portion of control module 139 may be implemented in an integrated circuit.

Leads 114, 115 include fixation elements 130A, 130B and 131. Fixation elements 130A and 130B may help locally fix electrodes proximate to target stimulation site, i.e., proximate the subclavian ansae nerve of a patient. In other examples, lead 115 may also include fixation elements located both proximally and distally to electrodes 151, or alternatively, lead 114 may only include fixation elements distal to electrodes 151. In other examples, leads 114 and 115 may include fixation elements at any suitable location along the length of lead bodies 148 and 149 to fix lead bodies 148 and 149 at various points between proximal ends 148A, 149A and distal ends 148B and 149B. The "length" is generally measured from the respective proximal end 148A, 149A to the respective distal end 148B, 149B of lead bodies 148 and 149.

As one example, an implantable signal generator or other stimulation circuitry within therapy delivery module 140 delivers electrical signals (e.g., pulses or substantially continuous-time signals, such as sinusoidal signals) to targets stimulation sites, including the subclavian ansae. For example, stimulation directed to the subclavian ansae may be blocking stimulation, such as a biphasic waveform. The stimulation may be applied as a continuous time waveform, as pulses, in response to a physiological condition of the patient or some combination thereof.

As an example, a stimulation program may instruct electrical stimulator 31 to generate a stimulation waveform having a current amplitude between about 1 milliamps and 100 milliamps, a voltage amplitude between about 0.1 volts and 10 volts, a pulse frequency between about 10 Hz and 800 Hz and/or a pulse width between about 20 microseconds and 800 microseconds. As another example, a stimulation program may instruct electrical stimulator 31 to generate a stimulation waveform having an amplitude of about 1 to 40 milliamps, or even 6 to 10, a frequency of about 10 to 500 Hz, and even 20 to 200 Hz, and a duration of about a few seconds to several minutes. The stimulation waveform may have a substantially square or spiked waveform. In some examples, a neurostimulation waveform may have a duty cycle in a range of about 15 to 25 percent, i.e., "on" for 15 to 25 percent of the time, and even 20 percent of the time. In other examples, a neurostimulation waveform may have a duty cycle in a range of about 50 to 100 percent, such as 75 to 100 percent or even 90 to 100 percent.

In other examples, a stimulation program may instruct stimulation generator 88 to generate a stimulation pulse; for example, a duration of about 20 to 800 microseconds, and even 80 to 120 microseconds may be used.

Electrical stimulator 31 may include a power source 147. Power source 147 may take the form of a small, rechargeable or non-rechargeable battery, or an inductive power interface that transcutaneously receives inductively coupled energy. In the case of a rechargeable battery, power source 147 similarly may include an inductive power interface for transcutaneous transfer of recharge power. In addition to a rechargeable battery, in some cases, power source 147 may include power supply circuitry to produce appropriate operating voltages and/or currents.

The stimulation energy generated by therapy delivery module 140 may be formulated as neurostimulation energy, e.g., for treatment of any of a variety of neurological disorders, or disorders influenced by patient neurological response. Also could be pacing, cardioversion and/or defibrillation. The signals may be delivered from therapy delivery module 140 to various, selected combinations of electrodes 150, 151 via a switch matrix and conductors carried by leads 114, 115 and electrically coupled to respective electrodes 150, 151.

Processor 142 may include one or more microprocessors, controllers, digital signal processors (DSPs), application specific integrated circuits (ASICs), field programmable gate arrays (FPGAs), discrete logic circuitry, or the like, or any combination thereof. Processor 142 controls the implantable signal generator within therapy delivery module 140 to deliver neurostimulation therapy according to selected stimulation parameters. Specifically, processor 142 controls therapy delivery module 140 to deliver electrical signals with selected amplitudes, pulse widths (if applicable), and rates specified by the programs. In addition, processor 142 may also control therapy delivery module 140 to deliver the neurostimulation signals via selected subsets of electrodes 150, 151 with selected polarities. For example, electrodes 150, 151 may be combined in various bipolar or multi-polar combinations, including combinations of electrodes on the same lead or different leads, to deliver stimulation energy to selected sites, such as nerve sites adjacent an occipital nerve, spinal column, pelvic floor nerve sites, or cranial nerve sites. Electrodes 150, 151 may also be combined in various bipolar or multi-polar combinations to deliver stimulation energy to selected sites, such as the subclavian ansea as well as other nerve sites, including nerve sites adjacent the spinal column, pelvic floor nerve sites, or cranial nerve sites. Electrodes 150, 151 may also be implanted to deliver cardiac therapy such as pacing, cardioversion and/or defibrillation.

Processor 142 may also control therapy delivery module 140 to deliver each signal according to a different program, thereby interleaving programs to simultaneously treat different symptoms or provide a combined therapeutic effect. For example, in addition to treatment of one symptom such as ventricular arrhythmias, electrical stimulator 31 may be configured to deliver neurostimulation therapy to treat other symptoms such as back pain. In such an example, electrodes 150 of lead 114 may be positioned to deliver stimulation therapy for treating one symptom, and electrodes 151 of lead 115 may be positioned to deliver stimulation therapy for treatment of another symptom.

Memory 144 of electrical stimulator 31 may include any volatile or non-volatile media, such as a RAM, ROM, NVRAM, EEPROM, flash memory, and the like. In some examples, memory 144 of electrical stimulator 31 may store multiple sets of stimulation parameters that are available to be selected via programmer 9 (FIG. 2) for delivery of stimulation therapy. For example, memory 144 may store stimulation parameters transmitted programmer 9 (FIG. 2). Memory 144 also stores program instructions that, when executed by processor 142, cause electrical stimulator 31 to deliver stimulation therapy according to selected programs or program groups. Accordingly, computer-readable media storing instructions may be provided to cause processor 142 to provide functionality as described herein.

Processor 142 may control telemetry module 146 to exchange information with an external programmer, such as programmer 9 (FIG. 2), by wireless telemetry. In addition, in some examples, telemetry module 146 supports wireless communication with one or more wireless sensors that sense physiological signals and transmit the signals to electrical stimulator 31, such as sensor 7 (FIG. 2).

Figure 8:
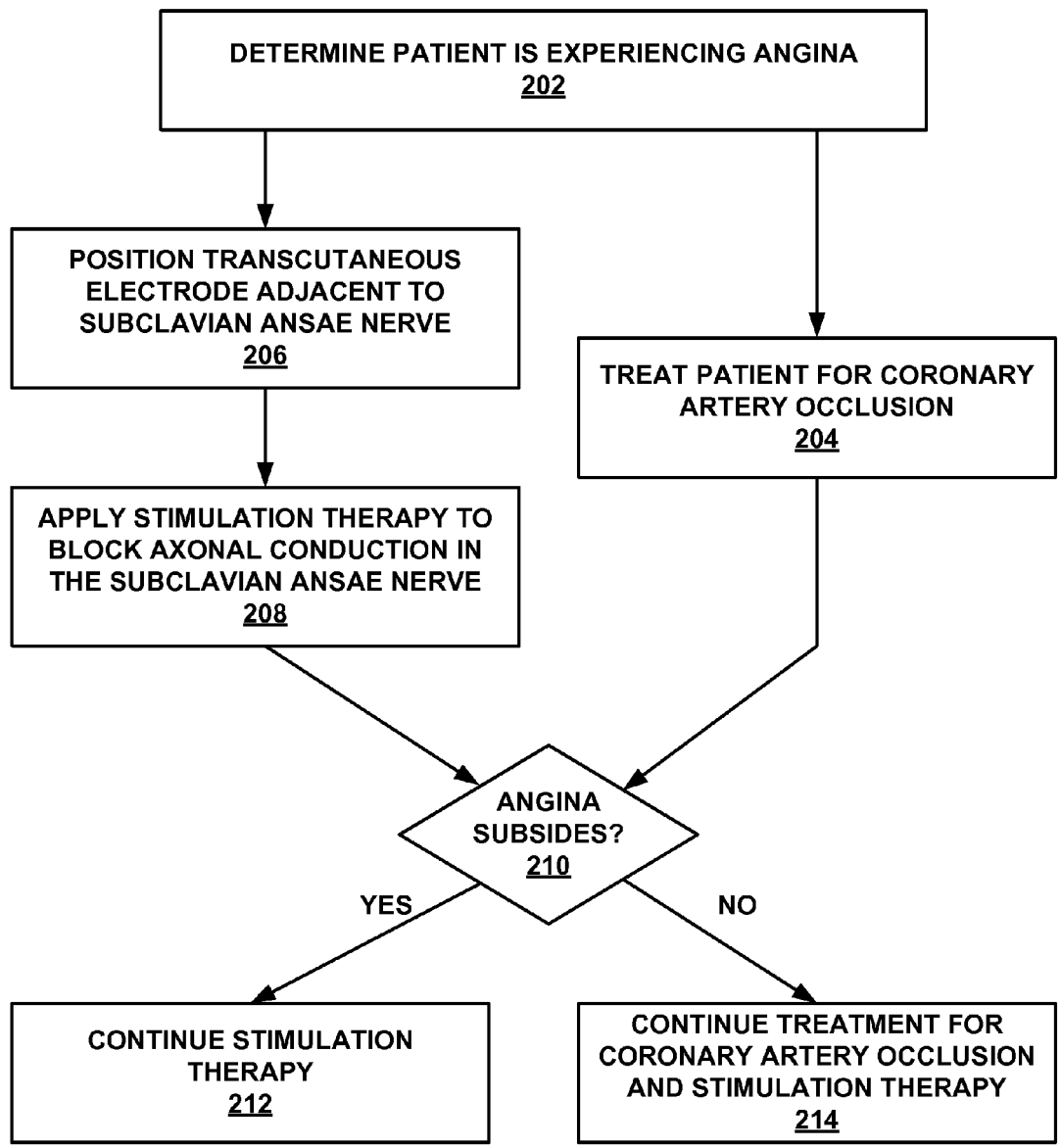
FIG. 8 is a flowchart illustrating example techniques for providing medical treatments including delivering stimulation therapy to a subclavian ansae nerve of a patient experiencing angina.

FIG. 8 is a flowchart illustrating techniques for providing medical treatments including delivering stimulation therapy to a subclavian ansae nerve of a patient experiencing angina. For clarity, the techniques shown in FIG. 8 are described with respect to transcutaneous stimulation system 20 (FIG. 1).

First a user, such as patient 10, a bystander, a first responder, paramedic or doctor, determines that patient 10 is experiencing angina pectoris (202). The clinician treats patient 10 for coronary artery occlusion, such as coronary artery occlusion associated with myocardial infarction (204). For example, treatment for coronary artery occlusion may include one or more of the following: performing an electrocardiogram (ECG), administering thrombolytic medication, administering beta blockers, administering Angiotensin-Converting Enzyme (ACE) inhibitors, administering an anticoagulant medication, administering an antiplatelet medication and administering a vasodilator. As one example, an ECG may be taken using stimulation generator 21 and lead 24 with electrodes 25 located on patient 10 as shown in FIG. 1.

While treating patient 10 for coronary artery occlusion, the clinician positions transcutaneous electrodes 23 proximate to area 12 and adjacent subclavian ansae nerve 13 (206). The stimulation generator 21 applies stimulation therapy via lead 22 to subclavian ansae nerve 13 (208). For example, the stimulation therapy may suppress sympathetic nervous system signals in patient 10 by blocking subclavian ansae nerve 13. Stimulation therapy signals suitable for blocking include high-frequency biphasic waveform signals.

Angina may indicate either coronary vasospasm or myocardial infarction in patient 10. If the angina subsides (210) as a result of the stimulation therapy, it may indicate that patient 10 is experiencing coronary vasospasm. In this case, the stimulation therapy should be continued (212). Alternatively, if the angina does not subside (210) as a result of the stimulation therapy, it may indicate that patient 10 is experiencing myocardial infarction. In this case, treatment for coronary artery occlusion should be continued (214). In either case, patient 10 should be given a clinical evaluation to definitively determine the cause of the angina.

Stimulation therapy of the subclavian ansae nerve 13 may also be continued if the angina does not subside as a result of the stimulation therapy. For example, simulation of the subclavian ansae nerve 13 may mitigate reperfusion damage in a myocardial infarction patient by slowing the rate of reperfusion following ischemia. As another example, stimulation of the subclavian ansae nerve 13 in a myocardial infarction patient may reduce the probability of ischemia-induced arrhythmias in the patient.

Figure 9:
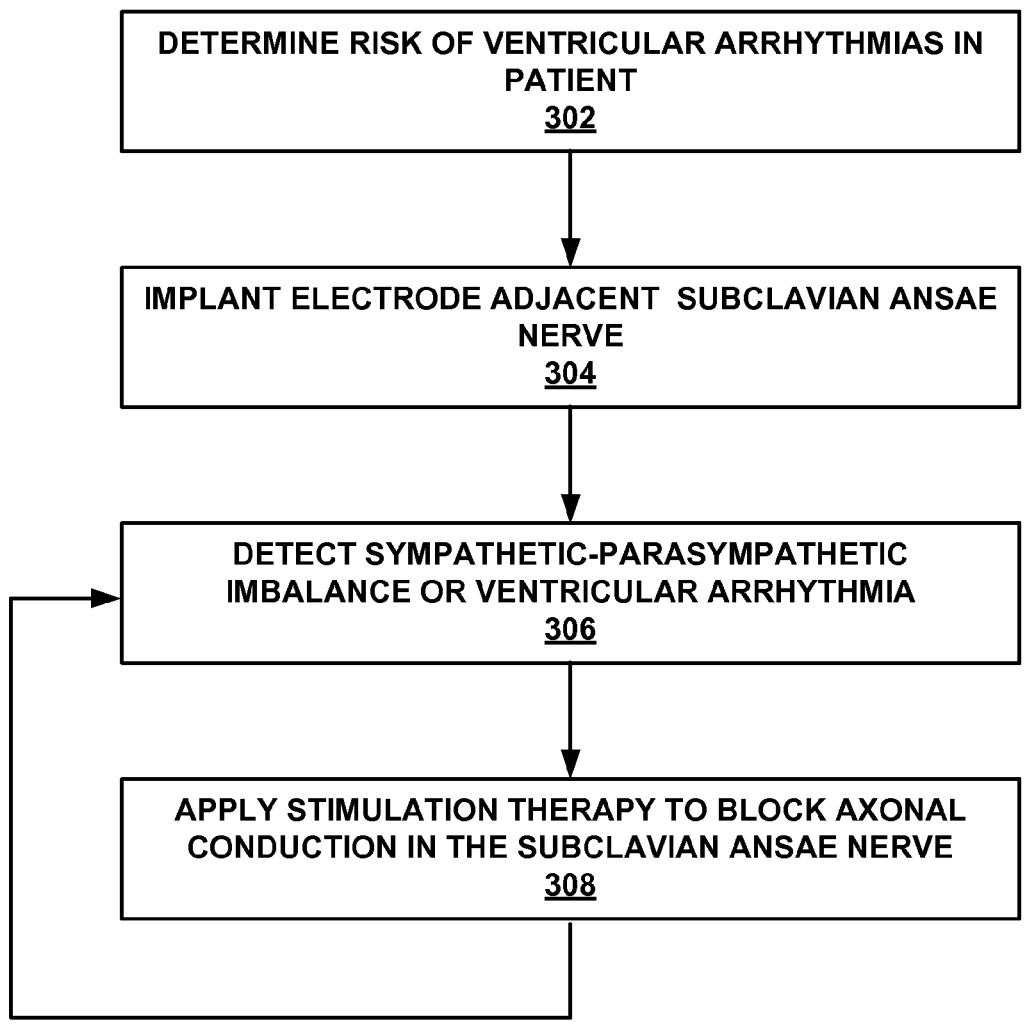
FIG. 9 is a flowchart illustrating example techniques for delivering stimulation therapy to a subclavian ansae nerve of a patient to limit ventricular arrhythmias in the patient.

FIG. 9 is a flowchart illustrating techniques for delivering stimulation therapy to a subclavian ansae nerve of a patient to limit ventricular arrhythmias in the patient. For clarity, the techniques shown in FIG. 9 are described with respect to implantable stimulation system 30 (FIGS. 2A-2B).

First, patient 10 is determined to be a candidate for implantation of IMD 31 to suppress sympathetic signals traversing subclavian ansae 13. For example, patient 10 may be a candidate for implantation if patient 10 has a risk of ventricular arrhythmias like VT and VF (302). Factors that may be considered in determining a risk of ventricular arrhythmias include, but are not limited to, a previous history of ventricular arrhythmias and/or a low injection fraction. Examples of low injection fractions include an injection fraction below 50 percent, an injection fraction below 40 percent, an injection fraction below 35 percent, an injection fraction below 30 percent, an injection fraction below 25 percent, an injection fraction below 20 percent and an injection fraction below 15 percent.

Next, lead 32 is implanted with electrode 34 in a position to deliver stimulation therapy subclavian ansae 13 (304). Lead 32 may be located to position electrode 34 adjacent subclavian ansae 13 using fluoroscopic imaging. IMD 31 is also implanted in patient 10, and lead 32 placed in electrical communication with IMD 31. Alternatively, lead 32 may be placed in electrical communication with a percutaneous stimulation generator. As previously described, a portion of lead 32 may be implanted within either a subclavian artery of patient 10 or subclavian vein 14. For example, lead may be implanted within subclavian vein 14 and stimulation electrode 34 may be advanced through a transvascular lumen in the subclavian vein 14 to an extravascular location adjacent subclavian ansae nerve 13.

Once implanted, a variety of techniques may be used to deliver stimulation therapy to subclavian ansae 13. For example, high-frequency biphasic waveform signals may be used to block the subclavian ansae. In general, stimulation therapy should inhibit the sympathetic nervous system in a patient to reduce incidence of ventricular arrhythmias. For example, IMD 31 may initiate stimulation therapy (308) following detection of ventricular arrhythmias like VT and VF (306) or coronary vasospasm in patient 10 using sensed physiological parameters of patient 10. As another example, IMD 31 may initiate stimulation therapy (308) following detection of an autonomic imbalance of the sympathetic and parasympathetic nervous systems (306). In addition, IMD 31 may generate blocking stimulation signals directed towards subclavian ansae nerve 13 according to a preprogrammed sequence, e.g., at regularly scheduled intervals.

Various examples of the invention have been described. These and other embodiments are within the scope of the following claims.

The invention claimed is:

1. A method comprising:
identifying a human patient as having angina; and
delivering stimulation therapy to a subclavian ansae nerve of a human patient with a stimulation electrode to limit sympathetic nervous system signals in response to identifying a human patient as having angina.

2. The method of claim 1, further comprising implanting the stimulation electrode within the patient.

3. The method of claim 2, further comprising implanting the stimulation electrode within one of a group consisting of: a subclavian artery of the patient; and a subclavian vein of the patient, wherein the stimulation electrode is disposed at a distal end of the medical lead.

4. The method of claim 2, wherein the stimulation electrode includes a transvascular electrode, the method further comprising implanting the transvascular electrode within a subclavian artery of the patient adjacent to the subclavian ansae nerve.

5. The method of claim 2, further comprising:
implanting a portion of a medical lead including the stimulation electrode within a subclavian vein of the patient; and
advancing the stimulation electrode through a transvascular lumen in the subclavian vein to an extravascular location adjacent the subclavian ansae nerve.

6. The method of claim 2, wherein implanting the stimulation electrode includes implanting a medical lead including the stimulation electrode while viewing the medical lead using fluoroscopic imaging.

7. The method of claim 1, wherein delivering the stimulation therapy includes delivering the stimulation therapy with an implantable stimulator via the stimulation electrode, the method further comprising implanting the stimulator within the patient.

8. The method of claim 1, wherein the stimulation electrode includes a transcutaneous electrode.

9. The method of claim 1, wherein delivering the stimulation therapy includes delivering the stimulation therapy with a stimulation electrode, wherein the stimulation electrode includes one of a group consisting of:
a nerve cuff electrode;
a transcutaneous electrode; and
a transvacular electrode.

10. The method of claim 1, wherein the stimulation therapy blocks axonal conduction in the subclavian ansae nerve.

11. The method of claim 1, wherein the stimulation therapy reduces sympathetic outflow to a heart of the patient.

12. A method comprising:
determining a human patient is experiencing angina pectoris; and
delivering electrical stimuli to a subclavian ansae nerve in the patient in response to the determination.

13. The method of claim 1, further comprising:
monitoring one or more physiological parameters of the patient;
positioning a stimulation field of the stimulation therapy to interact with the subclavian ansae nerve based on the monitored physiological parameters.

14. The method of claim 13, wherein the monitored physiological parameters include at least one of a group consisting of:
sympathetic tone;
parasympathetic tone;
an electrocardiogram (ECG);
heart rate;
QRS width;
atrioventricular (AV) dissociation;
respiration rate;
respiratory volume;
core temperature;
diaphragmatic stimulation;
skeletal muscle activity;
blood oxygen level;
cardiac output;
blood pressure;
intercardiac pressure;
time derivative of intercardiac pressure (dP/dt);
electromyogram (EMG) parameters; and
an electroencephalogram (EEG) parameters.

15. The method of claim 1, wherein the cardiac condition includes a naturally-occurring affliction selected from a group consisting of:
ventricular arrhythmias;
ventricular tachycardia (VT);
ventricular fibrillation (VF); and
coronary vasospasm.

16. The method of claim 12, wherein the stimulation therapy comprises high-frequency biphasic waveform signals.

17. The method of claim 12, further comprising treating the patient for occlusion of a coronary artery while blocking the transmission of the neurological signals on the subclavian ansae nerve.

18. The method of claim 17, wherein treating the patient for occlusion of a coronary artery includes one or more of a group consisting of:
generating an electrocardiogram (ECG);
administering thrombolytic medication;
administering beta blockers;
administering Angiotensin-Converting Enzyme (ACE) inhibitors;
administering an anticoagulant medication;
administering an antiplatelet medication; and
administering a vasodilator.

19. The method of claim 12, further comprising determining that the patient is experiencing naturally-occurring coronary vasospasm.

20. The method of claim 12, further comprising determining that the patient is experiencing naturally-occurring myocardial infarction.

21. A medical system comprising:
a set of one or more electrodes;
a stimulation generator coupled to the electrodes; and
a processor configured to determine a presence of angina and the processor further configured to control the stimulation generator to generate a stimulation therapy signal configured to at least partially block neural activity in a subclavian ansae nerve in a patient to treat the angina, and deliver the stimulation therapy signal via the set of electrodes.

22. The medical system of claim 21, wherein the stimulation therapy at least partially blocks axonal conduction in the subclavian ansae nerve.

23. The medical system of claim 21, wherein the stimulation therapy includes high-frequency biphasic currents to block axonal conduction in the subclavian ansae nerve.

24. The medical system of claim 21, wherein the set one or more electrodes includes at least one of a group consisting of:
a nerve cuff electrode;
a transcutaneous electrode; and
a transvacular electrode.

25. The medical system of claim 21, wherein the set of electrodes is a first set of electrodes, wherein the stimulation therapy is a first stimulation therapy, the system further comprising a second set of one or more electrodes, wherein the processor is configured to deliver a second stimulation therapy to the patient via the second set of electrodes, wherein the second stimulation therapy includes one of a group consisting of:
cardiac pacing therapy;
cardioversion therapy; and
defibrillation therapy.

26. The medical system of claim 21, wherein the patient is a human.

27. A medical device comprising:
means for determining a human patient is experiencing angina pectoris;
means for generating a stimulation therapy signal configured to at least partially block neural activity in a subclavian ansae nerve in response to determining the human patient is experiencing angina pectoris; and
means for delivering the stimulation therapy signal to the subclavian ansae nerve in a patient.

28. A method comprising:
determining that a patient is experiencing angina;
positioning a transcutaneous electrode near subclavian ansae nerve tissue;
stimulating the subclavian nerve tissue through the transcutaneous electrode; and
determining whether the angina subsided.

29. A method for treating a patient suffering from angina pectoris, the method comprising delivering, transcutaneously, electrical stimulation therapy to a subclavian ansae nerve in the patient, the stimulation therapy suppressing sympathetic nervous system signals by blocking transmission of neurological signals on the subclavian ansae nerve.

30. The method of claim 29, further comprising treating the patient for occlusion of a coronary artery while blocking the transmission of the neurological signals on the subclavian ansae nerve.

31. A method comprising:
monitoring a first set of one or more physiological parameters of the patient correlating to a sympathetic tone of a sympathetic nervous system of the patient;
monitoring a second set of one or more physiological parameters of the patient correlating to a parasympathetic tone of a parasympathetic nervous system of the patient;
identifying a human patient as having angina in response to monitoring one of the first and second set of one or more physiological parameters;
and
delivering the stimulation therapy to the subclavian ansae nerve based on identifying the human patient as having angina.

32. The method of claim 31, wherein monitoring the first set of physiological parameters includes monitoring a neurological ganglion of the patient.

33. The method of claim 31, wherein monitoring the second set of physiological parameters includes monitoring a vagus nerve of the patient.

34. A method comprising:
identifying a human patient as having angina; and
delivering stimulation therapy to a sympathetic nerve of a human patient with a stimulation electrode in response to identifying a human patient as having angina.

* * * * *